United States Patent

Noss et al.

Patent Number: 4,699,884
Date of Patent: Oct. 13, 1987

[54] PROCESS AND APPARATUS FOR THE SIMULTANEOUS APPLICATION OF A MULTIPLICITY OF LIQUID SAMPLES TO AN OBJECT STAGE

[76] Inventors: Gerhard Noss, Bruchholzweg 3, 3006 Burgwedel; Alois Höft, Elsternweg 4, 3201 Algermissen, both of Fed. Rep. of Germany

[21] Appl. No.: 797,323
[22] PCT Filed: Feb. 25, 1985
[86] PCT No.: PCT/DE85/00058
§ 371 Date: Oct. 21, 1985
§ 102(e) Date: Oct. 21, 1985
[87] PCT Pub. No.: WO85/03886
PCT Pub. Date: Sep. 12, 1985

[30] Foreign Application Priority Data

Feb. 29, 1984 [DE] Fed. Rep. of Germany ....... 3407849

[51] Int. Cl.⁴ .............................................. C12M 1/00
[52] U.S. Cl. .................................... 435/287; 435/294; 435/30; 435/300; 73/863; 222/420; 422/100
[58] Field of Search ............... 435/294, 293, 287, 301, 435/300, 298, 29, 30, 240; 73/863, 32; 222/420, 422; 422/100, 70

[56] References Cited

U.S. PATENT DOCUMENTS

| 2,533,089 | 12/1950 | Brewer et al. | 435/287 X |
| 2,643,801 | 6/1953 | Kollmeyer | 222/420 |
| 3,164,304 | 1/1965 | Jager et al. | 222/420 X |
| 3,785,928 | 1/1974 | Kessler | 435/287 X |
| 3,843,053 | 10/1974 | Thoden | 422/70 X |
| 4,058,370 | 11/1977 | Suovaniemi | 422/100 |
| 4,115,200 | 9/1978 | Anderson | 435/30 X |
| 4,246,339 | 1/1981 | Cole et al. | 422/100 X |
| 4,286,637 | 9/1981 | Wilson | 422/100 X |

FOREIGN PATENT DOCUMENTS 2116886 12/1971 Fed. Rep. of Germany.

Primary Examiner—Samuel Scott
Assistant Examiner—H. A. Odar
Attorney, Agent, or Firm—Donald C. Feix; T. M. Freiburger

[57] ABSTRACT

The invention relates to a process and an apparatus for the simultaneous application of a multiplicity of liquid samples to an object stage (2), more especially of sera to an object stage overgrown with cell cultures. In this connection, according to the invention the liquid samples are pressed with the aid of a multipipette (3) through a funnel plate (4), which rests immovably on the object stage (2) and which has a multiplicity of funnel-shaped containers (5) disposed side by side in a plane. The funnel plate (4) is then preferably left on the object stage (2) overgrown with cell cultures, until such time as incubation of the applied serum has taken place. By means of the process according to the invention, running of the sera is avoided and handling in a simple and reliable manner for the purposes of the laboratory investigation is guaranteed.

13 Claims, 6 Drawing Figures

PROCESS AND APPARATUS FOR THE SIMULTANEOUS APPLICATION OF A MULTIPLICITY OF LIQUID SAMPLES TO AN OBJECT STAGE

The invention relates to a process for the simultaneous application of a multiplicity of liquid samples to an object stage, more especially of sera on an object stage overgrown with cell cultures, as well as to an apparatus for carrying out the process.

For the purposes of the microscopic investigation of antibodies, attached to antigens of a cell culture, from an applied serum, it is known to provide an object stage of the standard size 26×76 mm or larger with applied cell cultures and to inoculate the latter with serum with the aid of a pipette. For this purpose, in many cases multipipettes are used, which permit the simultaneous application of a multiplicity of serum samples. With the aid of these multipipettes, the cell cultures themselves can also be applied to the object stage in advance.

It requires a high degree of concentration and skill to apply the cell cultures in a relatively close pattern to an object stage and then to inoculate these centrally in each instance with a serum. Moreover, by reason of the unequal height of the outlet tips of the multipipette, the result is a nonuniform distribution on the object stage. In order to prevent the serum from running from one cell culture to the next, it is accordingly known to cover the object stage with a protective layer, preferably of teflon, with a multiplicity of recesses in which a cell culture is situated in each instance. The use of object stages covered with a protective layer does indeed facilitate the handling and protection against running, but the application of the protective layer to the object stage cannot be undertaken by the test laboratories themselves and for this reason it is necessary to use expensive object stages which have already been coated. Object stages which are commercially available and which are provided with a protective layer exhibit in addition the disadvantage that their protective layer reacts with sensitivity to certain cleaning fluids, more especially acetone, and can therefore only be used to a restricted extent.

The application of object stages which are not covered with a protective layer sets narrow limits for application in the case of the abovementioned investigation, since the spacings of the cell cultures applied to the object stage must be chosen to be very large in order to prevent running, so that the application of object stages of such a kind is uneconomic.

From U.S. Pat. No. 377,699, an arrangement is indeed known which permits a regular application of a liquid in very small quantities to an object stage; however, since no protective layer is employed on the object stage, in this instance the problem of running is not corrected. The application of the liquid takes place in this instance in depressions which are upwardly open. Since the individual drops accordingly fall on to the object stage from a determined height, running of the drops cannot be ruled out. This is all the more possible, as the minimum quantity of fluid which can be applied with this device exceeds 25 $\mu L$.

The object of the invention is to indicate a process for the simultaneous application of a multiplicity of liquid samples to an object stage, in which the liquid samples can be disposed at a small spacing beside one another on the object stage, without running taking place between them. A further object of the invention is to indicate an apparatus for carrying out the process, which can be handled in a simple manner and which can be produced cheaply and which is adapted to the particular requirements of the laboratory investigation. A further object consists in indicating an object stage which is prepared in such a manner that a sequential investigation of sera can be carried out quickly, accurately and reliably.

The object of the invention is fulfilled by the invention indicated in the claims. Advantageous refinements of the invention are indicated in subclaims, the description and the drawings.

The process according to the invention permits a very rapid and reliable application of a multiplicity of liquid samples to an object stage, as is desirable more especially in the case of the sequential investigation of blood sera for the formation of antibodies. The process steps of the invention can be carried out without particular skill, since the stage plate which is employed has the function of a funnel and thus facilitates the accurate centering of a multipipette. For the performance of the process, use can be made of any object stage selectable at will, which does not need to exhibit any protective layer whatsoever. However, in the performance of the invention use can preferably be made of an object stage which is already coated with a standardized cell culture. In this case, a particularly rapid investigation of the blood sera to be investigated is possible.

The invention is explained hereinafter with reference to an exemplary embodiment. The figures show particular representations and embodiments of the invention.

In medical test laboratories, the investigation of blood sera for antibodies forms a part of the everyday work. The determination of the formation of antibodies takes place in general inter alia by means of techniques involving fluorescence microscopy. For this purpose, object stages are overgrown with a cell culture, to which blood sera are then applied in a quantity of 10-20 $\mu L$. After the expiry of an incubation period, the result can be determined.

In the process according to the invention, in the first instance an object stage, which exhibits for the simultaneous investigation of a multiplicity of samples preferably a size of 80×120 mm, is in the first instance coated with a multiplicity of cell cultures. The cell culture can be applied either to the entire object stage uniformly in a thin layer or at points at equal spacings. The second method is in general more economic, since in the application of the sera a spatial separation of the various serum samples is necessary, and in the intermediate spaces the presence of cell cultures is accordingly superfluous and uneconomic. The process according to the invention can likewise with advantage be employed for the purpose of the application of the cell cultures to the object stage.

Figure 1:
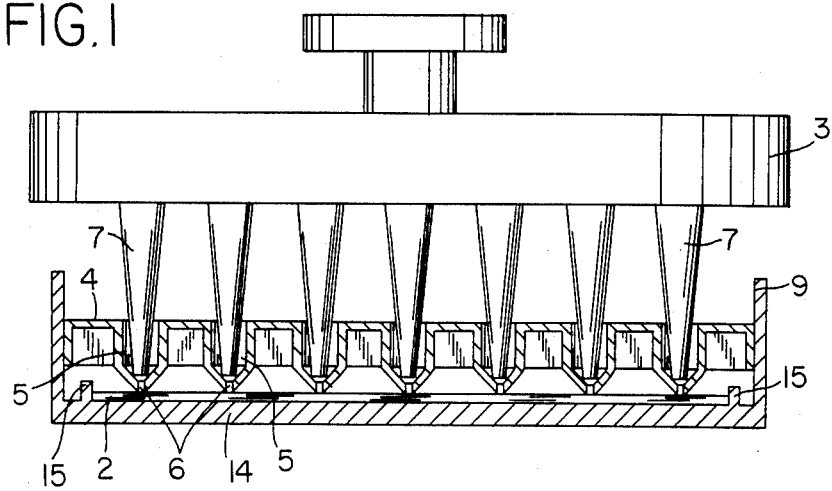
FIG. 1 shows an apparatus according to the invention.

FIG. 1 shows the apparatus according to the invention for carrying out the process. The object stage 2 is situated, to this end, between webs 15 on the base plate 14 of the box-shaped holder 9. Accordingly, the object stage 2 is fixedly disposed in an immovable manner within the holder 9. The funnel plate 4, which is described in greater detail below, is laid on the object stage 2. This funnel plate 4 contains a multiplicity of funnel-shaped containers 5, which become narrower in a downward direction and the lower surfaces of which, which converge to form a tip, rest on the object stage 2. A predetermined quantity of liquid may pass through the apertures 6 facing the object stage 2 with the aid of a multipipette 3, the flexible outlet tips 7 of which are brought on to the floor of the containers 5, by activation of the multipipette through each of the outlet apertures 6. The quantity of liquid which has passed through the outlet apertures 6 is distributed on the object stage plate in a circular configuration about the outlet apertures 6. After removal of the funnel plate 4, the cell cultures applied in this manner to an object stage 2 grow within a few days to the required size.

After cleaning of the funnel plate 4, the latter can possibly be used again, in order with the aid of the multipipette 3 to transfer blood sera to the cell cultures present on the stage plate.

Figure 2:
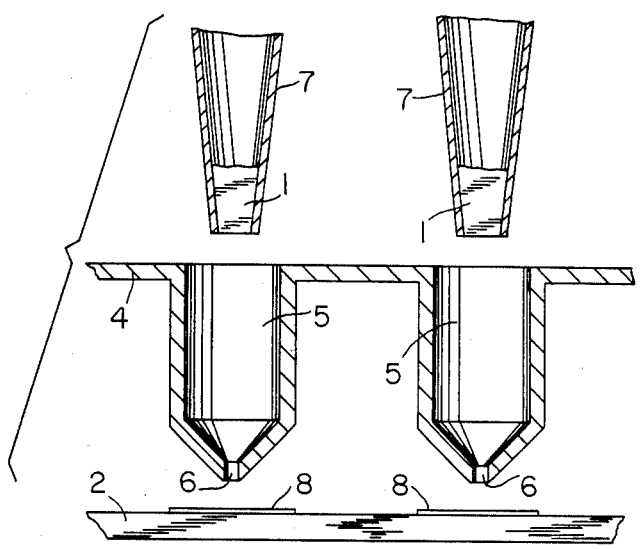
FIG. 2 shows a section from FIG. 1 in order to illustrate the positions of the arrangements employed for the process.

FIG. 2 shows the arrangement—represented one above the other—of object stage 2, stage plate 4 and outlet tips 7 of the multipipette 3 in enlarged representation. In this connection, the outlet tips 7 contain liquid samples 1, more especially a serum. The stage plate 2 exhibits cell cultures 8, to which the outlet apertures 6 of the stage plate 4 can be applied. After application of the stage plate 4 to the object stage 2 and introduction of the multipipette 7 into the containers 5 of the funnel plate 4, the liquid sample 1 can be applied through the outlet aperture 6 to the cell culture 8.

Figure 3:
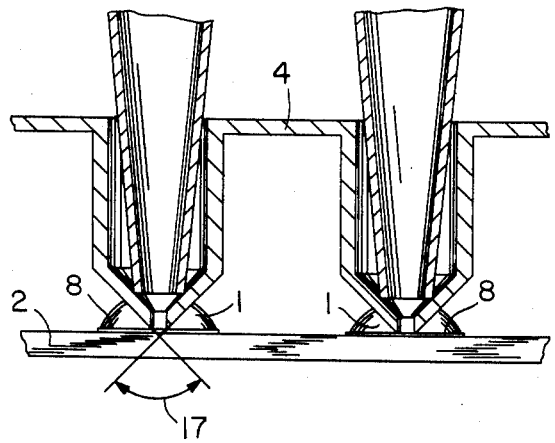
FIG. 3 shows a representation of the outlet procedure of the liquid samples.

FIG. 3 shows a representation which shows how a liquid sample 1 is transferred to the cell culture 8. It is shown that the liquid sample is situated between the cell culture 8 and the outer wall of the lower surface of the funnel plate 4. Accordingly, the cell culture 8 can be incubated directly by the serum. By diffusion of antibodies which are contained in the serum on to the antigens within the cell cultures, incubation takes place, which requires a period of time between approximately half an hour and three hours. This incubation preferably takes place by joint displacement of the object stage 2 and of the funnel plate 4—fixed by the holder 9—in an incubator. In this manner, the condition as represented in FIG. 3 can be achieved, namely the condition in which the liquid samples bulges (sic) between the cell culture 8 and the wall of the stage plate 4. On this basis, the serum is prevented from flowing to the adjacent cell culture. On the other hand, in this manner the spacing of the adjacent cell cultures can be kept very small, without there being any fear of a transfer from one cell culture to the other. After completion of the incubation, the excess serum is washed away.

In a particular embodiment of the invention, the object stage 2 which is employed is already an object stage which is provided with a standard cell culture and which is stored for a long period of time under conditions which are necessary for this purpose, more especially the observance of particular temperatures. If such an object stage 2 is disposed (sic) cell cultures 8 in the pattern which corresponds to the funnel plate 4, it is not necessary for rapid investigations to permit growth of a cell culture in each instance, which can then only be used after a certain period of time.

Figure 4:
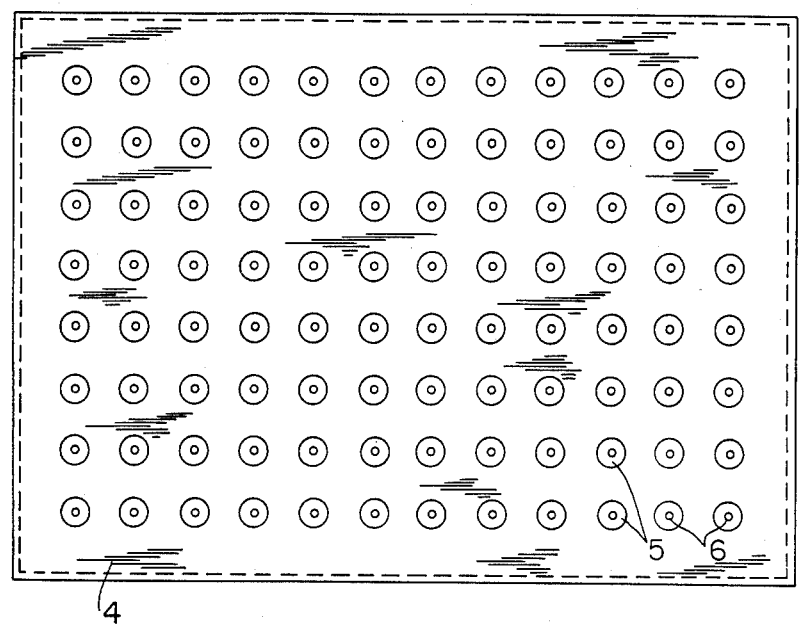
FIG. 4 shows a plan view of a stage plate.

FIG. 4 shows a plan view of a funnel plate 4. In U.S. Pat. No. 3,356,462, a plate with a corresponding arrangement of containers is indeed already indicated, but this plate represented therein serves to receive liquids for micro-titration. The funnel plate 4 according to the invention is distinguished from the arrangement according to the U.S. patent specification principally in that the containers in the case of the invention are perforated at their lower vertex. Accordingly, in the case of the invention the containers 5 serve as inlet funnels for the multipipette 3 which is employed. A flexible foil similar to the U.S. Pat. No. 3,356,462 is indeed also known, which has a multiplicity of perforated containers and which serves for the transfer of a multiplicity of liquid samples into the containers according to the U.S. patent specification in the course of the titration. The flexibility of the foil as well as the wall thickness and shape of the passage apertures do however prevent application for the purposes of the invention. As a result of the flexible construction of the foil, the latter cannot rest uniformly on a plane base, so that liquid could emerge only where the depressions of the foil are in contact with the base. However, in the case of the application of the foil for the transfer of micro-volumes into a plate according to U.S. Pat. No. 3,356,462, this is not important. A uniform, reliable application of micro-volumes to a plane glass surface is accordingly not possible with such an arrangement.

A funnel plate with an outlet opening which is situated in the same plane for all containers is accordingly essential for the purposes of accurate metering. This is achieved more especially by a fixed funnel plate. As a result of a particular design of the aperture angle 17 of the lower section—which tapers in a V—shaped configuration—of the otherwise cylindrical container, there is created on the object stage 2 the particular bulging—represented in FIG. 3—of the liquid sample 1. The angle 17 should preferably amount to more than 90°. In one practical embodiment, the angle amounted to approximately 120°.

The bore or stamping passing through the tips of the containers exhibits an approximately cylindrical configuration and is in a particular embodiment of the invention not deburred at its outer surface, but exhibits there a certain roughness, in order to facilitate the lateral emergence of the liquid 1 in the case of direct contact of the funnel plate 4 with the object stage 2. In one particular embodiment of the invention, the funnel plate 4 exhibits a grid of 8×12=96 containers.

Figure 5:
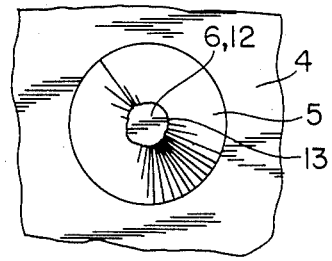
FIG. 5 shows a bottom plan view of a container.
Figure 6:
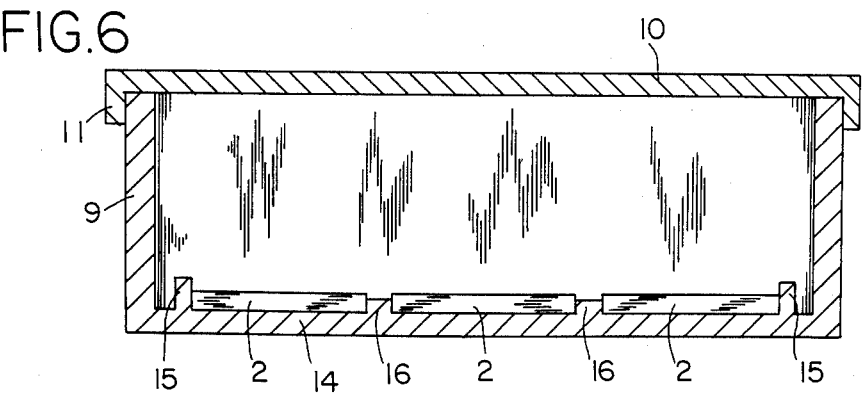
FIG. 6 shows a side elevation of a holder.

FIG. 5 shows the roughened edge of the bore 13 on the lower surface of the container 5.

In order also to be able to use object stages of smaller size in the arrangement according to the invention, the base plate 14 of the holder 9 further webs 16 are present, which prevent mutual displacement of smaller object stages 2. If the webs 15 which limit a large object stage laterally are designed to be somewhat higher than the further webs 16, the holder 9 can be employed for both sizes of object stages. In the event of the use of a large object stage, the latter rests on the further webs 16 and is limited by the laterally higher webs 15. On the other hand, smaller object stages 2 rest between the webs 16 or 16 and 15 respectively.

A lid-like attachment is preferably provided, which protects the object stage in the holder 9 from external influences on insertion into the incubator.

The invention is not restricted to application in the technology of medical testing; indeed, colored markings may also for example be applied to printed circuit boards in the electronics industry by the process according to the invention, or chemical products may also be produced locally.

LIST OF REFERENCE NUMERALS EMPLOYED

1: Liquid sample
2: Object stage
3: Multipipette
4: Funnel plate
5: Container
6: Outlet aperture
7: Outlet tip
8: Cell culture
9: Holder
10: Cover
11: Rim
12: Bore
13: Edge of the bore
14: Base plate
15: Web
16: Further webs
17: Aperture angle

We claim:

1. A process for simultaneously transferring a multiplicity of small liquid samples from a multipipette to a plane object stage surface without barriers to separate samples while maintaining the samples separated apart at small lateral spacings without merging on the plane surface of the object stage, said method comprising, holding the object stage having its plane upper surface fixedly disposed in an immovable manner in a holder, placing a funnel plate having a multiplicity of funnel shaped containers with inner surfaces, each converging to form a tip with an orifice at its lower end, in position on the object stage with each of the tips engaged with the plane upper surface of the object stage, said funnel plate having a sufficiently strong and rigid construction so as to cause all of the tips to make contact with the plane surface and at relatively close spacings between the tips, introducing outlet tips of a multipipette containing liquid samples into related tips of the funnel plate until the tips of the multipipette substantially engage the inner surfaces of the tips of the funnel plate to thereby directly apply and to transfer each of the liquid samples from the multipipette through the orifices of the funnel plate tips and to the locations on the plane upper surface of the object stage engaged by the tips of the funnel plate for an ensureed transfer of each sample and a transfer without a dripping or dribbling which could cause running together or merging of the samples on the object stage.

2. The process as claimed in claim 1, wherein prior to the application of the liquid samples (1) the object stage (2) is coated with a cell culture (8).

3. The process as claimed in claim 2, wherein the funnel plate (4) is left in its position relative to the object stage (2) until such time as an adequate penetration of the liquid samples (1) with the cell culture (8) has taken place.

4. The process as claimed in claim 2, wherein the liquid samples (1) are blood sera.

5. The process as claimed in claim 3 or 4, wherein the object stage (2) and the funnel plate (4) are left in position relative to one another until the cultures (8) are incubated by molecules present in the liquid samples.

6. The method defined in claim 1, wherein the said object stage is covered with a multiplicity of laterally spaced cell cultures (8) and wherein the liquid samples contain serum.

7. The method defined in claim 1, wherein the spacing as well as the arrangement of the cell cultures (8) correspond to the spacing and the arrangement of the outlet apertures (6) of the funnel plate (4), so that in each instance an outlet aperture (6) is associated with a respective cell culture (8).

8. Apparatus for carrying out a process of a type in which a multiplicity of small liquid samples are simultaneously transferred from a multipipette to a plane object stage surface while the samples are maintained separated apart at small lateral spacings without merging on the plane surface of the object stage, said apparatus comprising, an object stage having a plane upper surface, a holder which holds the object stage in an immovable manner within the holder, a funnel plate having a multiplicity of funnel shaped containers, each of whichconverges to form a tip with an orifice at its lower end, placed to engage each of the tips with the plane upper surface of the object stage, said funnel plate having a sufficiently strong and rigid construction so as to cause all of the tips to make contact with the plane surface and at small lateral spacing between tips, a multipipette having multiple outlet tips containing small quantities of a liquid sample and constructed to permit each multipipette outlet tip to be introduced into a related tip of the funnel plate until all the multipipette tips engage inner surfaces of the funnel plate tips and to thereby directly apply and transfer each of the liquid samples from the multipipette through the orifices of the funnel plate tips and to locations on the plane upper surface of the object stage engaged by the tips of the funnel plate for an ensured transfer of each sample and a transfer without a dripping or dribbling which could cause running together or merging of the samples on the object stage.

9. The invention defined in claim 8, wherein the holder (9) is constructed in a box-shaped configuration.

10. The invention defined in claim 8, wherein the funnel shaped containers (5), from the upper surface (11) of the funnel plate (4), are designed in the first instance in a cylindrical configuration and then so as to taper in a V shape, with the orifice comprising a cylindrical bore in the lower tip.

11. The invention defined in claim 10, wherein the edge (13) of the bore is roughened at the outer surface of the tip.

12. The invention defined in claim 8, wherein the holder has a base plate (14) and wherein webs (15) for the lateral fixing of an applied object stage (2) are provided on the base plate (14) of the holder (9).

13. The invention defined in claim 12, wherein further webs (16) are provided on the base plate (14) in order to subdivide the contact surface, in order to permit the disposition side by side of several object stages (2) which are smaller than the total surface of the base plate (14).

* * * * *